United States Patent [19]

Broadnax, Jr.

[11] Patent Number: 4,626,253
[45] Date of Patent: Dec. 2, 1986

[54] SURGICAL HEMOSTAT COMPRISING OXIDIZED CELLULOSE

[75] Inventor: Cecil H. Broadnax, Jr., Somerset, N.J.

[73] Assignee: Johnson & Johnson Products, Inc., New Brunswick, N.J.

[21] Appl. No.: 657,997

[22] Filed: Oct. 5, 1984

[51] Int. Cl.$^4$ ............................................. A61L 15/00
[52] U.S. Cl. ................................... 604/374; 128/156; 128/325
[58] Field of Search .............. 128/334, 335, 155, 156, 128/325; 536/56; 604/362, 358

[56] References Cited

U.S. PATENT DOCUMENTS

| | | | |
|---|---|---|---|
| 3,364,200 | 1/1968 | Ashton et al. | 536/56 |
| 3,666,750 | 5/1972 | Briskin | 128/156 |
| 3,937,223 | 2/1976 | Roth | 604/372 |
| 4,452,245 | 6/1984 | Usher | 128/334 R |

OTHER PUBLICATIONS

J. J. Press, Man-Made Textile Encyclopedia, Textile Book Publishers, Inc., 1959, pp. 456–466.

*Primary Examiner*—Dalton L. Truluck
*Attorney, Agent, or Firm*—Wayne R. Eberhardt

[57] ABSTRACT

A surgical hemostat comprising oxidized cellulose having a warp knit tricot construction which provides a fabric density of at least 0.03 g/cm$^2$, air porosity of less than 150 cm$^3$/sec/cm$^2$, and liquid absorption of at least 3 times the dry weight of the fabric.

9 Claims, No Drawings

SURGICAL HEMOSTAT COMPRISING OXIDIZED CELLULOSE

This invention relates to surgical hemostats for control of bleeding, and more particularly, to a knitted fabric of oxidized cellulose having superior handling and hemostatic properties.

The control of bleeding is a serious problem in certain surgical procedures and in various types of emergency wounds. Bleeding from the kidney, brain or liver or the persistent oozing from severed capillaries and veins, for example, is particularly difficult to control by conventional means such as suturing or ligature, and in many cases, is serious enough to endanger life. Surgical hemostats consisting of conventional gauze pads or similar articles impregnated with a hemostatic material such as ferric chloride, thrombin or the like have been used for many years to arrest bleeding. Hemostats of this type cannot be left in a closed wound, however, since foreign body tissue reaction would result.

Absorbable hemostatic materials have been developed which may be left in a wound site, if necessary, to control bleeding and will be eventually absorbed by the body without adverse tissue reaction. Such absorbable materials include the polymers and copolymers of lactide and glycolide, and oxidized cellulose. The preparation and use of oxidized cellulose as an absorbable heostat is disclosed in U.S. Pat. No. 3,364,200, the teachings of which are specifically incorporated herein by reference.

Briefly stated, U.S. Pat. No. 3,364,200 discloses the preparation of oxidized cellulose by treating bright rayon regenerated cellulose with an oxidizing agent such as dinitrogen tetroxide in a Freon medium. After oxidation, the fabric is thoroughly washed with a solvent such as carbon tetrachloride followed by aqueous solution of 50 percent isopropyl alcohol and finally, with 99 percent isopropyl alcohol. Prior to oxidation, the hemostat is constructed in the desired form such as a gauze, knit, woven fabric, felt or integrated mass of staple fibers. Example 1 of U.S. Pat. No. 3,364,200 describes the preparation of a hemostatic surgical gauze from 1.6 denier continous filament bright rayon. The rayon is first converted into a 90 filament, 150 total denier yarn and, thereafter, knitted on a Wildman 28 cut, spring needle knitting machine into a fabric of plain jersey construction having a weight of about 1 pound per 13 square yards and a count of 18 courses and 18 wales per linear inch.

The knit jersey fabric prepared according to the teachings of U.S. Pat. No. 3,364,200, particularly Example 1 thereof, is a lightweight open mesh material which conforms nicely to the surface configuration of the wound site and is effective in controlling bleeding. The present invention, however, is directed to an improved hemostatic material, also constructed of oxidized cellulose, which is more efficacious in controlling bleeding than the material of U.S. Pat. No. 3,364,200 and has other improved properties as well.

SUMMARY

The absorbable hemostatic materials of the present invention are warp knitted tricot fabrics constructed of bright rayon yarn which is subsequently oxidized by known techniques. The fabrics are characterized by having a single ply thickness of at least 0.5 mm, a density of at least 0.03 g/cm$^2$, air porosity of less than 150 cm$^3$/sec/cm$^2$ and liquid absorption capacity of at least 3 times the dry weight of the fabric and at least 0.1 water per cm$^2$ of the fabric at least 0.09 g water per cm2 of the fabric.

The knit fabrics of the present invention have good bulk without undue weight, are soft and drapable, conforming well to the configuration of the surface to which they are applied. The fabric may be cut into suitable sizes without running or fraying along the cut edge. Fabric strength after oxidation is more than adequate for use as a surgical hemostat.

The hemostatic properties of the fabric of the present invention are superior to those of the prior art knit fabrics. In addition, the increased bulk of the fabric of the instant invention allows the fabrics to be used singly-ply rather than folded as is necessary with the prior art fabrics.

DESCRIPTION OF PREFERRED EMBODIMENTS

The improved hemostatic fabrics of the present invention comprising oxidized cellulose are best characterized by their physical properties of thickness, bulk, porosity and liquid absorption capacity as recited above. Suitable fabrics having these properties may be constructed by knitting 60 denier, 18 filament bright rayon yarn on a 32 gauge machine at a knit quality of 12. A suitable tricot fabric construction is front bar 1-0, 10-11; back bar 2-3, 1-0. The extended shog movement imparted to the front bar results in a 188 inch runner compared to a 70 inch runner for the back guide bar and increases the fabric bulk and density. The ratio of front to back bar runners in this particular construction is 1:2.68.

The physical properties and the hemostatic efficacy of the fabric produced as above described were compared to those of the prior art knit fabric described in Example 1 of U.S. Pat. No. 3,364,200 with the following results:

TABLE I

| Property | This Invention | U.S. Pat. No. 3,364,200 |
| --- | --- | --- |
| Thickness, mm | 0.645 | 0.264 |
| Density, g/cm$^2$ | 0.052 | 0.017 |
| Air Porosity, cm$^3$/sec/cm$^2$ | 62.8 | >250 |
| Tensile Strength[1] (md/cd) Kg | 1.9/4.5 | 1.6/0.04 |
| Elongation, %[2] | 23/49 | 48/45 |
| Absorption[3] | | |
| g/g fabric | 3.88 | 3.20 |
| g/cm$^2$ fabric | 0.20 | 0.05 |
| Hemostasis,[4] min. | | |
| 1 ply | 5.7 ± 1.0 | No Test |
| 2 ply | 5.6 ± 1.8 | 6.8 ± 1.9 |
| 4 ply | No Test | 6.6 ± 1.3 |

[1] tensile strength determined at 2 in/min extension md/cd = machine direction/cross direction.
[2] Elongation, machine direction/cross direction.
[3] Absorption base on weight of water absorbed by fabric.
[4] Hemostasis evaluation on incised porcine splenic wounds, time to stop bleeding.

The tricot fabrics of the present invention may be constructed from bright rayon yarns of from about 40 to 80 total denier. Each yarn may contain from 10 to 25 individual filaments although each individual filament is preferably less than 5 denier to avoid extended absorption times.

The high bulk and fabric density are obtained by knitting at 28 gauge or finer, preferably at 32 gauge, with a fabric quality of about 10 or 12 (40 to 48 courses per inch). A long guide bar shog movement of at least 6 needle spaces, and preferably 8 to 12 spaces, further increases fabric thickness and density.

Other warp knit tricot fabric constructions which produce equivalent physical properties may, of course, be utilized in the manufacture of the improved hemostatic materials of the present invention, and such constructions will be apparent to those skilled in the art.

What is claimed is:

1. A surgical hemostat comprising a warp knit tricot fabric constructed of yarns of oxidized cellulose, said yarns being derived from bright rayon yarns of about 40 to 80 total denier, said fabric having a density of at least 0.03 g/cm$^2$, air porosity of less than 150 cm$^3$/sec/cm$^2$, and liquid absorption of at least 3 times the dry weight of the fabric and at least 0.1 g water per cm$^2$ of fabric.

2. The hemostat of claim 1 wherein said bright rayon yarn contains from 10 to 25 filaments.

3. The hemostat of claim 2 wherein said yarn contains 18 filaments and has a total denier of 60.

4. The hemostat of claim 3 wherein said tricot fabric has a density of about 0.05 g/cm$^2$, air porosity of about 60 cm$^3$/sec/cm$^2$ and liquid absorption of about 3.8 times the dry weight of the fabric.

5. A surgical hemostat comprising a warp knit tricot fabric constructed of oxidized cellulose yarn of about 40 to 80 denier, said fabric having a density of at least 0.03 g/cm$^2$, air porosity of less than 150 cm$^3$/sec/cm$^2$, and liquid absorption of at least 3 times the dry weight of the fabric and at least 0.1 g water per cm$^2$ of fabric.

6. The hemostat of claim 5 wherein the knit construction is as follows:
front bar 1-0, 10-11
back bar 2-3, 1-0
and the ratio of back bar to front bar runners is about 2.7.

7. The hemostat of claim 6 wherein the front bar runner is about 190 inches and the back bar runner is about 70 inches.

8. The hemostat of claim 6 having a density of about 0.05 g/cm$^2$, air porosity of about 60 cm$^3$/sec/cm$^2$, and liquid absorption of about 3.8 times the dry weight of the fabric.

9. The hemostat of claim 6 wherein said tricot fabric is a 32 gauge, 12 inch quality fabric.

* * * * *